United States Patent
Broadwin et al.

[11] Patent Number: 6,159,176
[45] Date of Patent: Dec. 12, 2000

[54] SHEATH AND SUPPORT FOR ULTRASONIC ELONGATE TIP

[75] Inventors: Alan Broadwin, Larchmont, N.Y.; Andrew Rushton, Milford, Conn.; Warren Erickson, Hopewell Junction, N.Y.; Daniel Grise, Brookfield, Conn.

[73] Assignee: Sonics & Materials Inc., Newtown, Conn.

[21] Appl. No.: 09/209,237

[22] Filed: Dec. 10, 1998

Related U.S. Application Data

[60] Provisional application No. 60/069,299, Dec. 11, 1997.

[51] Int. Cl.[7] .............................. A61B 17/20; A61B 17/32
[52] U.S. Cl. .............................................. 604/22; 606/169
[58] Field of Search ............................. 604/22; 606/167, 606/169–171, 180

[56] References Cited

U.S. PATENT DOCUMENTS

| | | | |
|---|---|---|---|
| 3,693,613 | 9/1972 | Kelman | 128/24 |
| 3,805,787 | 4/1974 | Banko | 128/276 |
| 3,956,826 | 5/1976 | Perdreaux, Jr. | 32/58 |
| 4,634,419 | 1/1987 | Kreizman et al. | 604/22 |
| 4,808,154 | 2/1989 | Freeman | 604/22 |
| 4,922,902 | 5/1990 | Wuchinich et al. | 604/22 |
| 5,123,903 | 6/1992 | Quaid et al. | 604/22 |
| 5,255,669 | 10/1993 | Kubota et al. | 128/24 AA |
| 5,322,055 | 6/1994 | Davison et al. | 601/2 |
| 5,628,743 | 5/1997 | Cimino | 606/1 |
| 5,810,859 | 9/1998 | DiMatteo et al. | 606/169 |
| 5,944,737 | 8/1999 | Tsonton et al. | 606/205 |

*Primary Examiner*—Sharon Kennedy
*Assistant Examiner*—Michael Hayes
*Attorney, Agent, or Firm*—St. Onge Steward Johnston & Reens LLC

[57] ABSTRACT

An improved ultrasonic surgical instrument is disclosed having a design that extends horn or tip life and minimizes instrument breakage and disintegration during use. The instrument comprises an ultrasonic tip having a distal working end and a metal sheath around the tip; the tip further having projections located in the vicinity of nodal points near the tip working end, said tip radially extending from the tip towards the sheath so as to provide the tip with radial inward support. The instrument can further comprise said tip with a substantially flat or convex end and said sheath with an inwardly projecting portion located distally of said tip projection and extending sufficiently radially inward so as to capture the tip with its projection should a tip break occur.

10 Claims, 1 Drawing Sheet

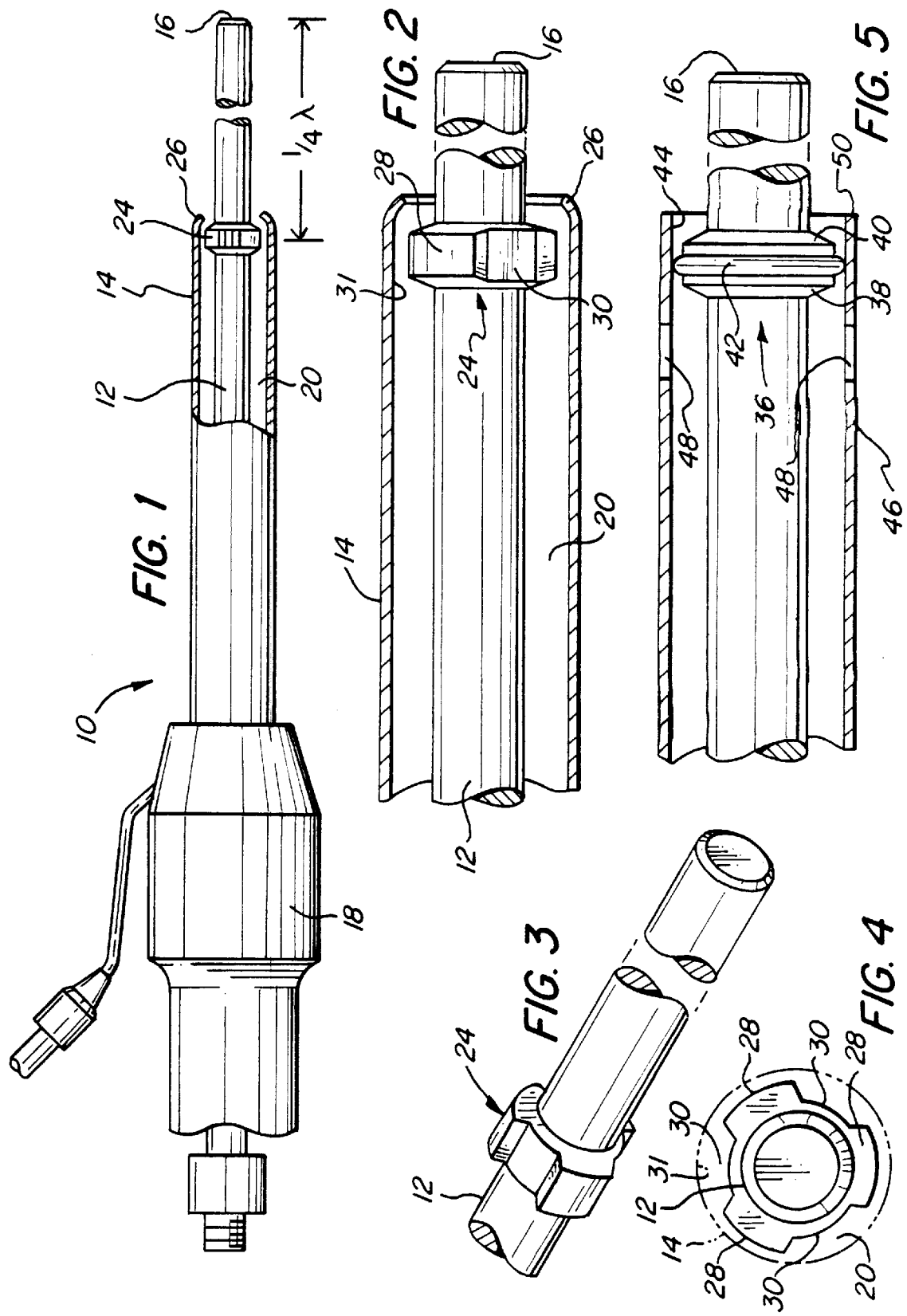

SHEATH AND SUPPORT FOR ULTRASONIC ELONGATE TIP

PRIOR APPLICATION

This application claims the benefit of U.S. Provisional Application No. 60/069,299 filed Dec. 11, 1997.

FIELD OF THE INVENTION

The present invention relates to ultrasonic surgical instruments useful in removing tissue from within a biological structure, and more particularly to an ultrasonic device employing an improved sheath and tip design allowing increased horn life and preventing instrument breakage and disintegration during use.

BACKGROUND OF THE INVENTION

Ultrasonic surgical instruments for minimally invasive procedures such as liposuction have been described in the prior art. Typically such instruments comprise an elongate tip or horn as these are commonly referred to, a sheath covering the horn, an irrigation source, a vacuum source, a transducer and a power supply. The ultrasonic surgical instruments generally employ piezoelectric or magnetostrictive transducers that transform high frequency electrical energy, i.e. greater than 20,000 Hz, into mechanical vibrations or impulses. The resultant longitudinal waves created are above the audible range and are thus "ultrasonic". The horn transmits these ultrasonic vibrations which when contacted with biological tissue such as fat, break down the cellular structure and allow removal via suction typically through a hollow tube formed inside the horn. In addition, the sleeve provides an annular space to supply irrigation fluid to the operative site and for cooling of the tip, the operating site and the sheath.

As explained in U.S. Pat. No. 5,123,903 (Quaid et al.), there is also a need to provide a sleeve or sheath around the tip to protect tissues from thermal damage due to abrasions from the proximal portions of the tip wherein the working part of the ultrasonic device, the end of the horn which contacts the tissue to be removed, is at the distal end of the tip. Such abrasions occur when the surgeon must direct the tip to a local area within a patient's body. As a consequence, lateral forces may be exerted on the horn particularly in liposuction or other minimally invasive applications where a long slender tip is needed. The result of such flexure is significant mechanical and thermal losses associated with less efficient transfer of mechanical energy to the tip of the device. In addition to efficiency losses, such lateral loading on the sheath and tip can cause rubbing and a scoring of the ultrasonic horn resulting in stress concentrations which can lead to cracking and shortened tip life.

The '903 patent addresses the problem of energy loss resulting from flexure by providing the plastic sleeve with inwardly projecting elements that are located so as to rest or contact the ultrasonic horn at a nodal point where longitudinal motion is at minimum. Alternatively, the '903 patent describes separate inserts which can be slipped over the horn and positioned at the vibratory nodes. The function of the supports is to maximize the transfer of energy to the tip of the horn and minimize undesirable energy transfer to the sleeve. The nodes are selected and are well known to be the points along the horn that produce the least vibration and are suited as a contact point between the sleeve and the horn.

In the aforementioned '903 patent, the sleeve is disposable and made of plastic, obviating the need for cleaning. However, the use of a plastic sleeve is not suitable for liposuction and minimally invasive surgery in that it tends to disintegrate from heating and vibration and thus may inject plastic particles into a patient where the particles can do harm. For example, burned plastic can be carcinogenic. Consequently, stainless steel is preferred. However, when a stainless steel sleeve is employed in the manner as taught by the '903 patent, the radially inwardly projecting elements, even though they are located at a nodal point, tend to score the horn. This scoring leads to stress points or lines and a subsequent cracking or breakage of the ultrasonic horn as previously described. It has been reported in the literature, that even with non sheath designs, ultrasonic tips have cracked and fallen into a patient during liposuction, resulting in at least a difficult retrieval situation during surgery. Even if the tip does not crack, the useful life of the tip is diminished because of the scoring at the nodes of the tip as a result of such contact. Such scoring can be accelerated by intentional contact with the support as taught by the '903 patent. If an annular ring is used that slips over the horn to contact the sleeve, significant mechanical and thermal losses can still occur due to the interface between the sleeve and horn. Moreover, the problem of fretting corrosion can occur at such an interface which can lead to further weakening of the integrity of the horn.

U.S. Pat. No. 4,6343,419 (Kreizman et al.) discloses an improved ultrasonic handpiece with an angled connecting body between the transducer and operative tip. The '419 patent discloses support means emanating radially from an inner wall of a support element to firmly hold the transducer in place. As with the '903 patent this arrangement does not solve the problem of scoring or weakening of the horn.

U.S. Pat. No. 3,956,826 (Perdreaux, Jr.) teaches the use of preferably a plastic outersleeve with a bore, annular groove, and a ring brazed onto the shaft of a horn at a nodal point. However, this approach does not solve the problem of fretting corrosion or efficiency loss from such an arrangement, and is designed so as to contact and support the sleeve from the horn.

U.S. Pat. No. 3,805,787 (Banko) describes an ultrasonic surgical instrument wherein a stainless steel sleeve surrounds the horn. The sleeve is suspended in cantilever fashion from a proximal end of the housing. However due to this type of support the problem of flexure still remains and scoring contact near the distal end of the sheath occurs.

A common disadvantage to the prior art is that the ultrasonic devices suitable for liposuction are not of a design that; a) reduces mechanical and thermal losses from flexure and dissipation, and b) adequately support a sleeve or sheath which protects the patient against undesirable thermal damage and abrasion of the horn while simultaneously preventing scoring and breakage of the tip along with capture should the tip break.

What is desired, therefore, is an ultrasonic device, particularly suitable for liposuction or minimally invasive procedures, which employs a design that will protect the patient from unwanted thermal damage and tissue abrasions due to lateral contact, reduce flexure, reduce efficiency losses, and prevent broken or disintegrated material associated with the device from entering the patient.

SUMMARY OF THE INVENTION

Accordingly, it is an object of the present invention to provide an ultrasonic device which protects against unwanted thermal damage and abrasions of tissue lateral to a targeted treatment area of the patient and which is constructed from materials that prevent broken or disintegrated matter associated with the device from entering the patient.

It is another object of the present invention to provide an ultrasonic device that reduces flexure, particularly with liposuction or other minimally invasive surgical applications, thereby improving the efficiency of energy transfer of long slender tips to the surgical site.

It is a further object of the present invention to provide an ultrasonic device designed to minimize contact of a protective sheath with an ultrasonic horn so as to reduce weakening and scoring of the horn due to friction and stress concentration from such contact, along with reducing the mechanical and thermal losses resulting from such contact.

Another object of the present invention is to provide an ultrasonic device of a design that allows the tip to be irrigated while providing a support for a protective sheath that minimizes efficiency losses and frictional heat generated from intimate contact with the ultrasonic horn, and prevents thermal damage to laterally adjacent tissue.

Yet another object of the invention is to provide an ultrasonic device having a tip with an extended useful life whereby any wear is directed to a surface external to the basic envelope of the tip so as not to affect the structural integrity of the tip.

A further object of the invention is to provide an ultrasonic device having a tip with an extended useful life whereby the tip can be economically resurfaced without affecting the operating parameters or surgical performance of the tip.

Still another object of the invention is to provide an ultrasonic device with a means for preventing the tip from falling into a patient in the event that the tip cracks and breaks while inserted during surgery.

To overcome the deficiencies of the prior art and to achieve the objects and advantages listed above, the present invention comprises: an ultrasonic tip having a distal working end and a metal sheath around the tip; the tip further having projections, depending on the length of the tip, located in the vicinity of the nodal points wherein the horn or tip may have more than one nodal point spaced at ½ λ intervals along the length of the tip. At least one of these nodal points being near the tip working end, and wherein said projection radially extends from the tip towards the sheath so as to provide the tip with radial inward support(s).

The invention in one of its aspects also provides a metal sheath with an inwardly projecting portion located distally of said distal tip projection such that the inwardly projecting portion extends sufficiently radially inward so as to capture the tip with its projection should breakage occur.

In another embodiment, the invention provides the tip projection with an O-ring, wherein said tip is provided with a pair of longitudinally spaced apart retainer elements positioned to retain said O-ring between them near said nodal point thereby achieving reduced flexure and efficiency loss while preventing direct contact of the sheath and horn.

In another aspect, the invention provides an ultrasonic tip with a substantially flat or convex end which can allow for multiple resurfacing without affecting the surgical performance.

The invention and its particular features and advantages will become more apparent from the following detailed description when considered with reference to the accompanying drawings.

BRIEF DESCRIPTION OF THE DRAWINGS

FIG. 1 is a side view, partially cut away, of an ultrasonic instrument or device in accordance with the invention.

FIG. 2 is an enlarged section view of the working end segment of the ultrasonic instrument as shown in the embodiment of FIG. 1.

FIG. 3 is a partial perspective view of the working end of the ultrasonic horn used in the embodiment of FIG. 1.

FIG. 4 is an axial end on view of the ultrasonic horn and the projection shown in FIG. 3.

FIG. 5 is an enlarged section view of another embodiment of the working end for an ultrasonic horn in accordance with the invention.

DETAILED DESCRIPTION OF THE INVENTION

With reference to FIGS. 1–4, one embodiment of the invention is illustrated wherein the ultrasonic instrument 10 has a horn or tip 12 surrounded by a sheath 14. The distal end 16 of the tip 12 is the working end of the instrument where the ultrasonic fragmentation of tissue occurs. The sheath 14 is affixed to the housing 18 of the instrument and defines with the tip 12 an annular space 20 through which material, such as irrigation liquid, can be injected at the surgical site near distal end 16. The ultrasonic tip 12 can be a solid form or have a hole forming a cannula to permit fragmented tissue to be removed via suction through the tip 12.

The ultrasonic tip 12 is provided with an annular ring type projection 24 integral in construction with tip 12 and located at a first nodal point from the tip end 16. This nodal point typically is at about ¼λ, the sonic wavelength of the material of the tip 12, from tip end 16. Additional projections 24 at other nodal points can be used. For a 21 KHz operating frequency, the nodal point is about 2½ inches from end 16. The location of the projection 24 may vary from the nodal point by as much as +/−2½% of λ.

The projection 24 can be annular or be formed of circumferentially spaced parts. Preferably, the projection 24 is constructed of the same material as tip 12 and is integral in construction with tip 12. It is desirable to place projection 24 within the annular space formed between sheath 14 and tip 12 so as to create a small clearance space for the passage of irrigation fluid for cooling and to minimize contact between the sheath 14 and tip 12 to avoid efficiency losses and flexure. A preferred material for tip 12 and projection 24 is titanium metal due to its low acoustic losses, particularly for the long length to diameter ratios suitable for endoscopic or laposcopic surgical applications such as liposuction. Projection 24 is shaped to radially support an end portion of sheath 14, which has its end 26 rolled over so as to be bent inwardly past the projection 24. The roll over of end 26 by the sheath 14 captures the portion of the tip 12 that is proximal of end 26 and thus enhances safety of the instrument against inadvertent breakage of tip 12 at higher stress points closer to housing 18. The rolled over end 26 thus extends radially inward by an amount sufficient to be below the raised segments 28 of the tip projection 24. A preferred material for sheath 14 is stainless steel of a grade suitable for surgical applications, however sheath 14 is not limited to such, and any material sufficiently rigid to protect tip 12 from flexure that is biocompatible can be used.

One advantage to the present invention is that projection 24 results in a significant increase in the life of the ultrasonic tip 12 as well as less likelihood that the tip will break off and "fall" into a patient during surgery due to rolled over end 26 of sheath 14. With such a projection 24, any wear or scoring of the tip 12 by virtue of a rubbing contact between the sleeve or sheath 14 and tip 12 is limited to a reinforced segment of the tip 12. In this manner any scoring arising from rubbing contact between the sleeve and tip is limited to the projection 24 and significantly reduces stress regions and any resulting breakage of the titanium horn or tip 12.

Another advantage to this aspect of the invention is that when the projection 24 is integral in construction to tip 12 there is no significant mechanical or thermal losses between any interface of tip 12 with projection 24 due to high operating frequencies associated with ultrasonic devices. There is also no problem of fretting corrosion as a result of the integral construction.

The projection 24 can be further shaped so that it has radially inward notches 30 bounded by radially raised segments 28, although the present invention is not limited to such. In a different embodiment, projection 24 can be an annular ring shape without any raised segments 28 or recessed segments 30. The recessed segments 30 enable more irrigation fluid or fragmented tissue to pass the projection 24 and thus move through the annular passage 20.

Note that the sheath 14 in FIG. 4 has a small passage between the raised segments 28 and the inner surface 31 of the cylindrical sheath 14. In practice this may not exist continuously and thus a contact between the sheath and horn may arise intermittently, but such contact is not desired as this will reduce efficiency and promote erosion. Any resulting scoring between the sheath and horn, however, can be tolerated since such scoring will be on the raised segments or on the sheath 14 and thus are unlikely to result in a breakage of tip 12.

FIG. 5 illustrates another embodiment of the present invention where a projection 36 is formed from a pair of annular longitudinally spaced segments 38, 40, preferably integrally constructed with tip 12 and sized to capture an O-ring 42 between them. The O-ring 42 is formed of an elastomeric or other polymeric material that is benign for surgical purposes and is designed to receive the inward surface 44 of a stainless steel sheath 46. Contact between O-ring 42 and sheath 46 is not required, and the present invention is not limited to such. The sheath 46 is provided with holes 48 located proximally of the projection 36 so as to enable the added injection of irrigation fluid. Note that the sheath 40 has no inwardly curved end 50, though this could be used if so desired.

One advantage to this embodiment is that direct metal to metal contact between tip 12 and sheath 46 is avoided as a result of O-ring 42. This allows any vibrational erosion to be absorbed by the O-ring 42, thereby preventing scoring of tip 12 or the sheath 46. In addition, O-ring 42 can be readily replaced as it wears, thereby extending the useful life of tip 12.

The resulting ultrasonic instrument or device 10 creates a constrained environment around the ultrasonic horn or tip 12 by the sheaths 14 or 46 to minimize undesirable flexural oscillations and also prevents continuous direct contact between the ultrasonic horn or tip 12, the sheath and the patient's surrounding lateral tissue. It also provides a means to capture a broken tip 12 as well as an annular space for irrigant to protect the surrounding tissue and keep it cool.

Note that in order to benefit from the longer life obtainable because of the sheath and nodal supports, the distal end 16 of the tip 12 has been designed nearly flat or convex so that it can be easily resurfaced to remove the imperfections caused by cavitation. This is additionally enabled when the tip 12 is coupled with a wide band ultrasonic generator which allows multiple resurfacing of the surgical tip without affecting performance.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. An ultrasonic instrument comprising:
    an ultrasonic tip having a distal end and a metal sheath around the tip;
    a tip projection mounted on the ultrasonic tip in the vicinity of a nodal point near the distal end extending radially outwardly towards and terminating at a distance from said sheath so as to reduce contact and scoring between said tip and said sheath, said O-ring projection having a raised segment and a notch so as to enable the passage of fluid through said notch and between said sheath and said tip, said tip projection being provided with a pair of longitudinally spaced apart retainer elements positioned to retain an O-ring between said retainer elements near said nodal point.

2. The ultrasonic instrument as claimed in claim 1, wherein said tip has an additional projection in the vicinity of another nodal point.

3. The ultrasonic instrument as claimed in claim 1, wherein said tip has a projection is located a distance of +/−2½% of an operating ultrasonic wavelength from said nodal points.

4. The ultrasonic instrument as claimed in claim 1, wherein said metal sheath has an inwardly projecting portion located distally of said tip projection and extending sufficiently radially inward so as to capture said tip projection with its projection portion.

5. The ultrasonic surgical instrument as claimed in claim 1, wherein said sheath is provided with fluid passages located on the proximal side of said tip projection.

6. The ultrasonic surgical instrument as claimed in claim 1, wherein said sheath is provided with fluid passages located on the proximal side of said tip projection.

7. The ultrasonic instrument as claimed in claim 1, wherein said tip projection is located a distance of +/−2½% of an operating ultrasonic wavelength from said nodal point.

8. The ultrasonic instrument as claimed in claim 1, wherein said tip has a substantially flat or convex end.

9. The ultrasonic instrument as claimed in claim 1, wherein said tip has a substantially flat or convex end.

10. An ultrasonic surgical instrument comprising:
    an ultrasonic tip having a distal end and a metal sheath around the tip;
    said tip further having a pair of longitudinally spaced apart retainer elements located in the vicinity of a nodal point near said distal end, each extending radially outwardly from the ultrasonic tip and terminating at a distance from the metal sheath; and
    an O-ring retained between said retainer elements and being peripherally in contact with the metal sheath.

* * * * *